United States Patent [19]

Ise

[11] Patent Number: 5,133,963

[45] Date of Patent: Jul. 28, 1992

[54] METHOD OF PRODUCING COMMERCIALLY USEFUL POULTRY PRODUCTS WITH INCREASED CONCENTRATIONS OF OMEGA-3 POLYUNSATURATED FATTY ACIDS

[76] Inventor: Shuntaro Ise, Ise-Foodsbuild 2-1-4, Negishi, Taito-ku, Tokyo, 110, Japan

[21] Appl. No.: 631,956

[22] Filed: Dec. 21, 1990

[51] Int. Cl.$^5$ .................. A61K 37/54; A61K 31/355; A61K 31/20
[52] U.S. Cl. ................ 424/94.61; 514/458; 514/560
[58] Field of Search ............... 514/560, 458; 424/94.61

[56] References Cited

U.S. PATENT DOCUMENTS

| | | | |
|---|---|---|---|
| 3,845,208 | 10/1974 | Grandadam et al. | 514/179 |
| 4,086,365 | 4/1978 | Snetsinger et al. | 426/2 |
| 4,128,640 | 12/1978 | Klein | 424/195.1 |
| 4,197,293 | 4/1980 | Klein | 424/195.1 |
| 4,197,294 | 4/1980 | Klein | 424/195.1 |
| 4,738,853 | 4/1988 | Horrobin | 426/2 |
| 4,880,639 | 11/1989 | Lauermann et al. | 426/2 |
| 4,908,218 | 4/1990 | Laurent et al. | 426/2 |
| 4,918,104 | 4/1990 | Weiss et al. | 514/560 |

FOREIGN PATENT DOCUMENTS 59-39258  3/1984  Japan .

OTHER PUBLICATIONS

Chemical Abstracts (103:214012z) 1985.

*Primary Examiner*—Frederick E. Waddell
*Assistant Examiner*—K. Weddington
*Attorney, Agent, or Firm*—Sixbey, Friedman, Leedom & Ferguson

[57] ABSTRACT

A method for increasing the concentration of Omega-3 polyunsaturated fatty acids in poultry products is provided. The method includes adding to ordinary poultry feed an excess of Omega-3 polyunsaturated fatty acids and Vitamin E and feeding this supplemented feed to poultry simultaneously with enriched water to produce commercially valuable quantities of poultry products high in Omega-3 polyunsaturated fatty acids.

9 Claims, 3 Drawing Sheets

FIG.1

METHOD OF PRODUCING COMMERCIALLY USEFUL POULTRY PRODUCTS WITH INCREASED CONCENTRATIONS OF OMEGA-3 POLYUNSATURATED FATTY ACIDS

TECHNICAL FIELD

The present invention relates generally to methods for affecting the content of edible animal products by controlling the animals' diet and specifically to a method for producing commercially useful quantities of poultry products with increased Omega-3 polyunsaturated fatty acids by feeding the poultry a diet formulated to transfer the increased Omega-3 polyunsaturated fatty acids to the poultry products.

BACKGROUND OF THE INVENTION

There is increasing concern today directed to the high blood lipid levels, especially cholesterol and triglycerides, experienced by a significant proportion of the population. Elevated blood lipids can be indicative of such potentially serious health problems as coronary artery disease. The relationship between blood lipid levels and fat consumption in the diet has been well-studied and extensively documented. Lowering blood lipids to minimize health problems almost always involves modifying the diet to decrease or substantially eliminate fat consumption. As anyone who has ever lived with such dietary restrictions knows well, limiting fat consumption is difficult. The fat content of many foods contributes to their good taste and satisfying mouth feel.

Medical and nutrition experts have discovered that the elimination of all fat from the diet is not necessarily helpful in lowering elevated blood lipid levels and promoting good health. Some fats, in particular, Omega-3 polyunsaturated fatty acids, have been demonstrated to have beneficial effects in reducing the risk of heart disease and other conditions. However, it is recommended by most health experts that not more than 30% of the calories consumed each day be derived from fat. Of the fat calories consumed, at least about 5% of these calories should come from Omega-3 polyunsaturated fatty acids and a like amount from other Omega polyunsaturated fatty acids, specifically Omega-6 polyunsaturated fatty acids. Maintaining a favorable balance between the consumption of Omega-3 and Omega-6 fatty acids appears to be very important. An excess of Omega-6 fatty acids can interfere with the beneficial effects of the Omega-3 fatty acids. The diets of most consumers tend to be higher in Omega-6 fatty acids, in part because Omega-6 fatty acid-containing foods are more readily available and are more palatable. Additionally, some Omega-3 polyunsaturated fatty acids are unstable and easily destroyed.

The oils from land-grown plants and the animals fed on such plants are high in Omega-6 fatty acids, and they form a large part of the average diet. Omega-3 fatty acids are available in comparable amounts from only a small number of land-grown food plants, including walnuts, flax-seed, rapeseed (the source of canola oil) and purslane. The best dietary sources of Omega-3 fatty acids are marine: fatty fish that live in very cold water, including mackerel, anchovies, herring, salmon, sardines, Atlantic sturgeon, tuna and lake trout. These fish contain between about 1,000 and 2,300 milligrams of Omega-3 polyunsaturated fatty acids in about 3 and one-half ounces of raw fish. Other fish are also good sources of Omega-3 fatty acids, however.

Unfortunately, despite the overwhelming evidence of the beneficial health effects to be realized by consuming high Omega-3 polyunsaturated fatty acid-containing fish, a large number of people find it very difficult to do so. Good, fresh fish may not be readily available. Many people, moreover, have never acquired a taste for fish or find it difficult to prepare because of the strong taste and smell which is associated with most fish that is not perfectly fresh. Cleaning fresh fish is a task that many find unpleasant and, as a result, they forego eating the fish they have caught unless they can find someone else to do the job. Consequently, there have been increasing efforts to increase the Omega-3 polyunsaturated fatty acid content of foods which are readily available and which a large number of consumers will prepare and eat.

One food that is appealing to a substantial proportion of the population is eggs, especially eggs from chickens. Eggs are nutritionally balanced, taste good, are easily obtained at reasonable cost and are easy to cook. However, eggs contain somewhat high amounts of cholesterol and other lipids and have been accused of increasing blood cholesterol levels when too many are eaten too often. Therefore, despite the high food value of hens' eggs, many medical practitioners and nutritionists recommend that their high cholesterol patients reduce significantly or eliminate completely this otherwise excellent food. Various egg substitutes with reduced cholesterol and lipids are available. Not only do these substitutes differ in many respects from real eggs, however, but they also do not contain any significant amounts of Omega-3 polyunsaturated fatty acids. Therefore, the beneficial effects derived from the consumption of foods, such as fish, which have high Omega-3 polyunsaturated fatty acid levels are not available with egg substitutes.

Increasing the Omega-3 polyunsaturated fatty acid concentration of poultry products, including eggs has been suggested by the prior art. U.S. Pat. No. 4,918,104 to Weiss et al., for example, describes a method of increasing the concentration of Omega-3 polyunsaturated fatty acids in poultry by administering to the poultry a preformed Omega-3 fatty acid or a metabolic precursor of an Omega-3 fatty acid. The Omega-3 fatty acid or precursor is added in high amounts to a specialty feed composition which is fed to broilers and laying hens. The method described in this patent is stated to produce increased Omega-3 polyunsaturated fatty acid levels in chicken meat and eggs. This result is achieved by a feeding method which feeds the chickens an unbalanced diet for a period of time sufficient to demonstrate an increase in Omega-3 polyunsaturated fatty acids in the meat and eggs. However, the feed composition and feeding method described in this patent are not useful on a commercial scale to produce, consistently, over an extended period of time a large, commercially valuable supply of chicken eggs and meat high in Omega-3 fatty acids.

The Omega-3 fatty acid source preferred in the method of U.S. Pat. No. 4,918,104 is menhaden oil, which imparts a somewhat fishy odor and taste to the poultry products produced according to the method described in this patent. As a result, only those consumers who are accustomed to eating fish are likely to find these products acceptable. Additionally, the feeding of broilers and laying hens the unbalanced diet disclosed in this patent as described is highly likely to lead to problems in the chickens that reduces significantly their commercial value. For example, chickens force fed a diet that is high in Omega-3 polyunsaturated fatty acids exhibit listlessness, molting, lack of appetite, abnormal digestion and weight loss and are generally dull and inactive. Laying hens fed such a diet, moreover, demonstrate reduced egg production. Consequently, the method of increasing Omega-3 polyunsaturated fatty acid levels in poultry eggs disclosed in U.S. Pat. No. 4,918,104 will not produce a sufficiently high egg yield for a commercially viable egg production operation.

The prior art, therefore, does not disclose a commercially useful method for increasing the Omega-3 polyunsaturated fatty acid concentration of eggs and other poultry products that can be used in actual commercial production to successfully produce a dependable commercially significant supply of high Omega-3 fatty acid-containing poultry products.

SUMMARY OF THE INVENTION

It is a primary object of the present invention, therefore, to overcome the disadvantages of the prior art and to provide a method for producing a dependable commercially significant supply of poultry products high in Omega-3 polyunsaturated fatty acids.

It is another object of the present invention to provide a commercially valuable method of producing large quantities of eggs with an increased concentration of Omega-3 polyunsaturated fatty acids.

It is a further object of the present invention to provide a commercially valuable method of producing chicken meat with an increased concentration of Omega-3 polyunsaturated fatty acids.

It is still a further object of the present invention to provide a method of producing commercially useful quantities of high Omega-3 polyunsaturated fatty acid-containing poultry products.

The aforesaid objects are accomplished by providing a commercially valuable method of increasing the Omega-3 polyunsaturated fatty acid content of poultry eggs and meat. The method of the present invention includes feeding poultry over an extended period of time a diet consisting of feed to which has been added about 1 to 5% Omega-3 polyunsaturated fatty acids and Vitamin E and separately feeding the poultry enriched water.

Other objects and advantages will be apparent from the following description, claims and drawings.

DETAILED DESCRIPTION OF THE PREFERRED EMBODIMENTS

The beneficial effects of Omega-3 polyunsaturated fatty acids have been widely acknowledged, and medical and nutrition authorities recommend the increased consumption of foods, such as fish, that are high in Omega-3 polyunsaturated fatty acids. The primary Omega-3 polyunsaturated fatty acids are eicosapentanoic acid (EPA) and docosahexanoic acid (DHA), which represent about 15% to 30% of the total oil or fat content, or about 1% to 6% of a fresh fish. The consumption of adequate amounts of Omega-3 polyunsaturated fatty acids, such as EPA and DHA, requires the consumer to eat relatively large amounts of fish, which is difficult for many. Fish tend to have large numbers of small bones, which makes obtaining the meat difficult. The characteristic odor of fish is also unappealing to many. Although fish oil supplements have been prescribed when medically indicated, such as in acute coronary artery disease, the ingestion of fish oil by the general population is not the recommended method of increasing Omega-3 polyunsaturated fatty acid intake. Increasing the Omega-3 polyunsaturated fatty acid content of other food, such as eggs and other poultry products, is a good way to provide the beneficial effects of Omega-3 fatty acids to consumers in a more palatable and generally acceptable form. The production of commercially useful quantities of high Omega-3 polyunsaturated fatty acid-containing poultry products, however, has not been possible heretofore.

According to the method of the present invention, poultry, especially broilers and laying hens, are fed a poultry feed containing a high Omega-3 polyunsaturated fatty acid content which effectively produces poultry meat and eggs with a high Omega-3 polyunsaturated fatty acid content. Unlike prior art methods of producing poultry products and eggs high in Omega-3 polyunsaturated fatty acids, however, the present method does not impart an unpleasant "fishy" odor to these foods. Additionally, the method of the present invention consistently produces a commercially valuable high Omega-3 fatty acid-containing food product in large quantities. Unlike prior art methods, the present method of feeding poultry does not adversely affect egg-laying production or capacity so that laying hens fed according to the present method have a higher survival rate and a significantly more effective egg production rate. The poultry products of the present invention, moreover, do not differ from products with naturally occurring levels of Omega-3 polyunsaturated fatty acids in smell or taste.

The feeding method of the present invention was discovered to avoid the problems observed to arise when poultry, particularly laying hens, are fed feed that is unbalanced or contains an especially high level of one ingredient. Although it is sometimes possible to produce poultry products, including eggs, which contain higher than normal levels of certain components or ingredients by feeding the chickens a feed containing an excessive amount of the desired component or ingredient, as discussed above, such an unbalanced diet leads to health problems in the chickens. Moreover, the high or excessive content of an ingredient in the feed does not guarantee that high levels of the ingredient will be transferred into the organs or products of the animal being fed the feed. The ingredient present in higher than normal levels in the feed may even affect the animal's digestion so that the ingredient is not absorbed. If the ingredient is absorbed, it may be eliminated by the animal and not transferred to the desired part of the animal. Consequently, the feed must also contain additional ingredients to promote the transfer of a specific component to the desired part of the animal.

Additionally, each ingredient in the egg will be present only up to a maximum limit and, as a result, increasing the feed concentration of an ingredient beyond what is required to produce the maximum limit of that ingredient in the egg may produce adverse effects in the hen. When hens are fed feed with large amounts of Omega-3 polyunsaturated fatty acids, loss of appetite, molting and a drastic decrease in egg production are observed before a higher than normal amount of Omega-3 fatty acids appears in the eggs. Although the transfer of Omega-3 polyunsaturated fatty acids to the eggs does occur, because of the adverse effects on egg production, it occurs at such a low rate that this is not a feasible or realistic method for producing commercially valuable quantities of eggs or even for producing a small supply of eggs.

The present invention overcomes the disadvantages of prior art Omega-3 polyunsaturated fatty acid feeding methods by providing a poultry feed composition high in Omega-3 polyunsaturated fatty acids and Vitamin E and an enriched water which is fed to the poultry separately so that the Omega-3 polyunsaturated fatty acids are absorbed by the chickens without creating digestive disorders or adverse physical or constitutional systems and transferred to the poultry meat and eggs. Optimally, the eggs of hens fed according to the present invention should contain at least 0.5 gram Omega-3 polyunsaturated fatty acids in each 100 grams of yolk. To achieve this, at least 1% by weight of Omega-3 polyunsaturated fatty acids must be added to the feed. However, the maximum amount of Omega-3 polyunsaturated fatty acid which will appear in the yolk is 0.5 gram per 100 grams of yolk, and amounts of Omega-3 polyunsaturated fatty acid beyond 5% by weight of the feed do not have any effect on this maximum amount. Therefore, the preferred additive level of Omega-3 polyunsaturated fatty acids is 1% to 5% by weight of the feed. The amounts of eicosopentanoic acid (EPA) and docosahexanoic acid (DHA) which can be produced in the egg according to the present invention are about 30 mg and 200 mg, respectively.

Generally, Omega-3 polyunsaturated fatty acids in the form of fish meal is not suitable as a poultry feed additive for the commercial production of broilers and eggs. The unpleasant odor characteristic of fish meal is transferred to the meat and the eggs and can be easily detected by the average consumer. Fish oil added to poultry feed tends to have a similar negative effect. Therefore, unless a deodorizing process is employed with these two sources of Omega-3 polyunsaturated fatty acids, products that are palatable to consumers will not be produced. A suitable source of Omega-3 polyunsaturated fatty acids, which is preferred for the process of the present invention is vacuum deodorized fish oil, particularly vacuum deodorized menhaden oil. This product, which is generally available from many government and commercial fisheries, is reliable in quality and does not have the "fishy" smell characteristic of most fish oil. A preferred vacuum deodorized mehaden oil has the following composition:

| | |
|---|---|
| EPA | 125.3 mg/g |
| DHA | 106.4 mg/g |
| Total n-3 | 316.3 mg/g |
| Free Fatty Acids | 0.05% |
| Cholesterol | 2.2 mg/g |

| -continued | |
|---|---|
| Peroxide Value | 0.38 meq/kg |
| Iodine Value | 186.6 |
| Anisidine Value | 37.9 |
| Antioxidant Content: | |
| a-Tocopherol | 1 mg/g |
| g-Tocopherol | 1 mg/g |
| TBHO | 0.26% |
| Moisture | 271 mg/g |
| PCB | <0.05 mg/g |
| Total DDT | <0.05 mg/g |
| Total Saturated Fats | 260.1 mg/g |
| Total Monoenes | 223.4 mg/g |
| Total Dienes | 32.9 mg/g |
| Total PUFA | 393.4 mg/g |
| Total n-3 | 316.3 mg/g |
| Total n-6 | 24.4 mg/g |
| n-3/n-6 | 13.0 |

The sensory attributes of this fish oil product were found to have the following values on a scale of 0 to 15, where 15 represents the maximum intensity:

| | |
|---|---|
| ODOR | |
| TIO | 3.75 |
| Buttery | 0 |
| Beany | 0.26 |
| Rancid | 0 |
| Painty | 0.35 |
| Oxidized | 0.02 |
| Brassy | 0 |
| Fishy | 1.72 |
| Bitter | 0 |
| Sweet | 0 |
| Fruity/Perfumy | 0.21 |
| Burnt | 0 |
| Decomposition | 0.21 |
| Cardboard | 0.04 |
| Solvent | 0.03 |
| FLAVOR | |
| TIF | 4.37 |
| Buttery | 0 |
| Beany | 0.27 |
| Rancid | 0.23 |
| Painty | 0.39 |
| Oxidized | 0.33 |
| Brassy | 0.15 |
| Fishy | 2.34 |
| Bitter | 0 |
| Sweet | 0 |
| Fruity/Perfumy | 0 |
| Burnt | nd |
| Acrid | nd |
| Decomposition | 0.28 |

The emulsification of fish oil and fish oil esters has been found to eliminate the fishy odor and also to promote the transfer of the Omega-3 polyunsaturated fatty acids from the hens' feed to the yolks of the eggs laid by hens fed with feed containing emulsified fish oil. One emulsoid form of Omega-3 polyunsaturated fatty acid-containing fish oil preferred for use in the present method includes fish oil or a fish oil ester emulsified by a gelatin-saccharine alcohol-water mixture. Other emulsions which substantially eliminate the "fishy" odor and promote transfer of the Omega-3 polyunsaturated fatty acids from fish oil or fish oil esters from the feed to the meat or eggs of poultry fed the feed could also be employed, however.

The feed should additionally contain about 0.7% by weight of Vitamin E. The addition of Vitamin E to poultry feed in conjunction with Omega-3 polyunsaturated fatty acids enhances the production of Omega-3 polyunsaturated fatty acid-containing eggs in commercially valuable quantities by hens fed this feed.

The undesirable side effects and adverse physical symptoms demonstrated by birds fed a diet very high in Omega-3 polyunsaturated fatty acids alone are eliminated by concurrently feeding the poultry a special water which is enriched with at least the following components:

| | |
|---|---|
| silicic acid | 0.369% |
| glucanase | 0.018% |
| cellulase | 0.004% |
| calcium | 0.006% |
| phosphorus | 0.001% |

About 120 grams of this enriched water is preferably administered to each bird per day.

A seventy-five week feeding test was conducted to compare the survival rate and egg productivity rate among three groups of hens. Each group initially included 100 pullets or laying hens. All three groups were fed what will be referred to as "Plain" feed. The "Plain" feed has the following composition:

| | |
|---|---|
| Corn and Milo | 58% |
| Soybean pulp (oil extracted); corn gluten meal; rapeseed pulp (oil extracted) | 19% |
| Fish meal; meat and bone (animal) meal | 8% |
| Corn gluten, feed grade | 2% |
| Calcium carbonate; animal fats; salt; calcium phosphate; paprika extracts; and | 13% |
| paprika pulp | |

To this mixture is added the following additives: Vitamin A, Vitamin $D_3$, Vitamin E, Vitamin $B_1$, Vitamin $B_{12}$, Pantothenic Acid, Nicotinic Acid, Biotin, Vitamin $K_3$, Folic Acid, Ferrous sulfate, Copper sulfate, Manganese sulfate, Zinc carbonate, Colbalt sulfate, Methionine, Calcium iodate, and Ethoxine. The foregoing feed composition provides a minimum metabolic energy of 2,930 calories per kilogram.

The first group of hens (Group 1) was fed only the plain feed described above. The second group of hens (Group 2) was fed this plain feed to which had been added about 5% of an Omega-3 polyunsaturated fatty acid-containing liquid. The third group of hens (Group 3) was fed the Omega-3 polyunsaturated fatty acid-containing feed fed to the second group to which had been added 0.7% by weight Vitamin E and was also fed the enriched water described above. Tables I, II and III below set forth data obtained during the feeding test relating to egg laying, productivity and survival for, respectively, the first, second and third groups of hens.

Figure 1:
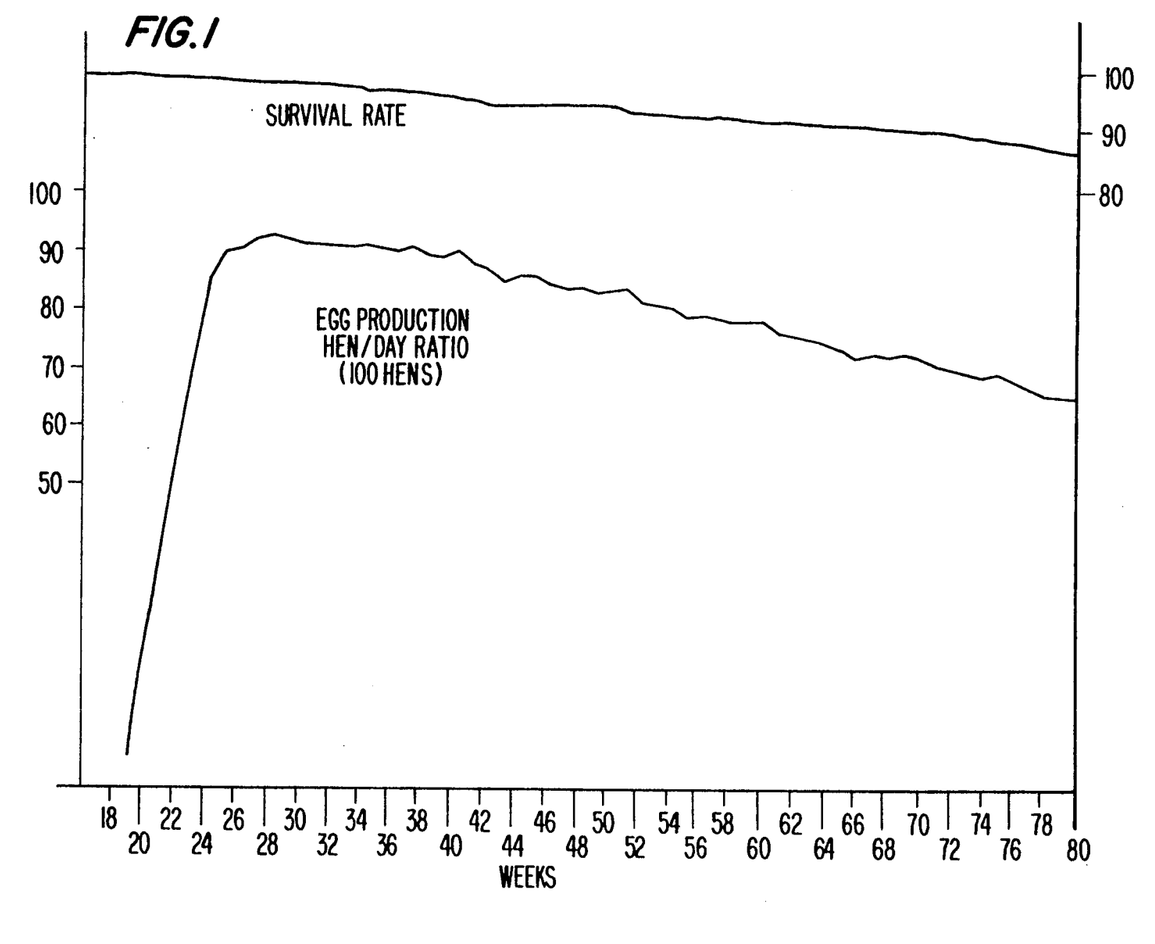
FIG. 1 illustrates graphically the survival rate and egg production of hens fed a plain poultry feed.
Figure 2:
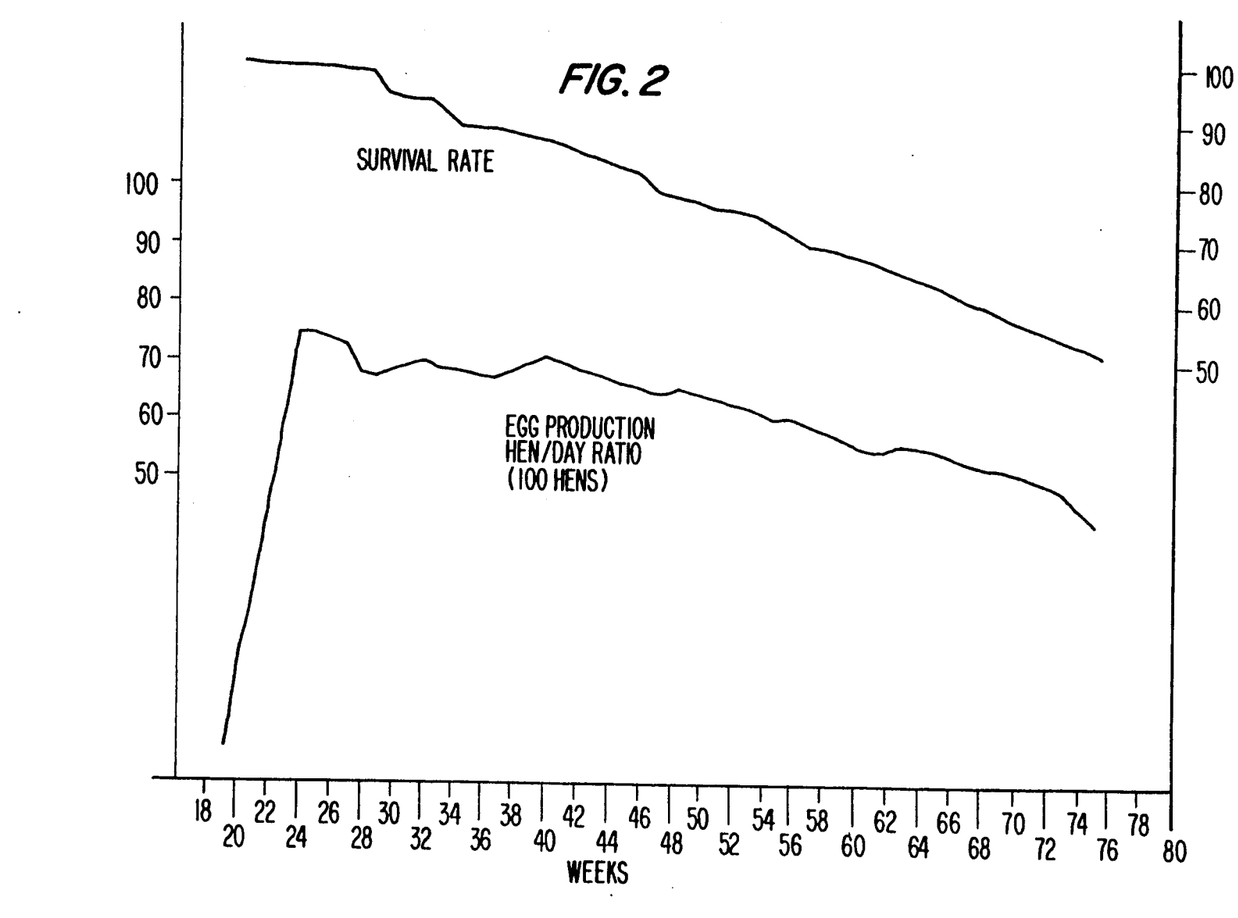
FIG. 2 illustrates graphically the survival rate and egg production of hens fed with a plain poultry feed to which has been added only a source of Omega-3 polyunsaturated fatty acids.
Figure 3:
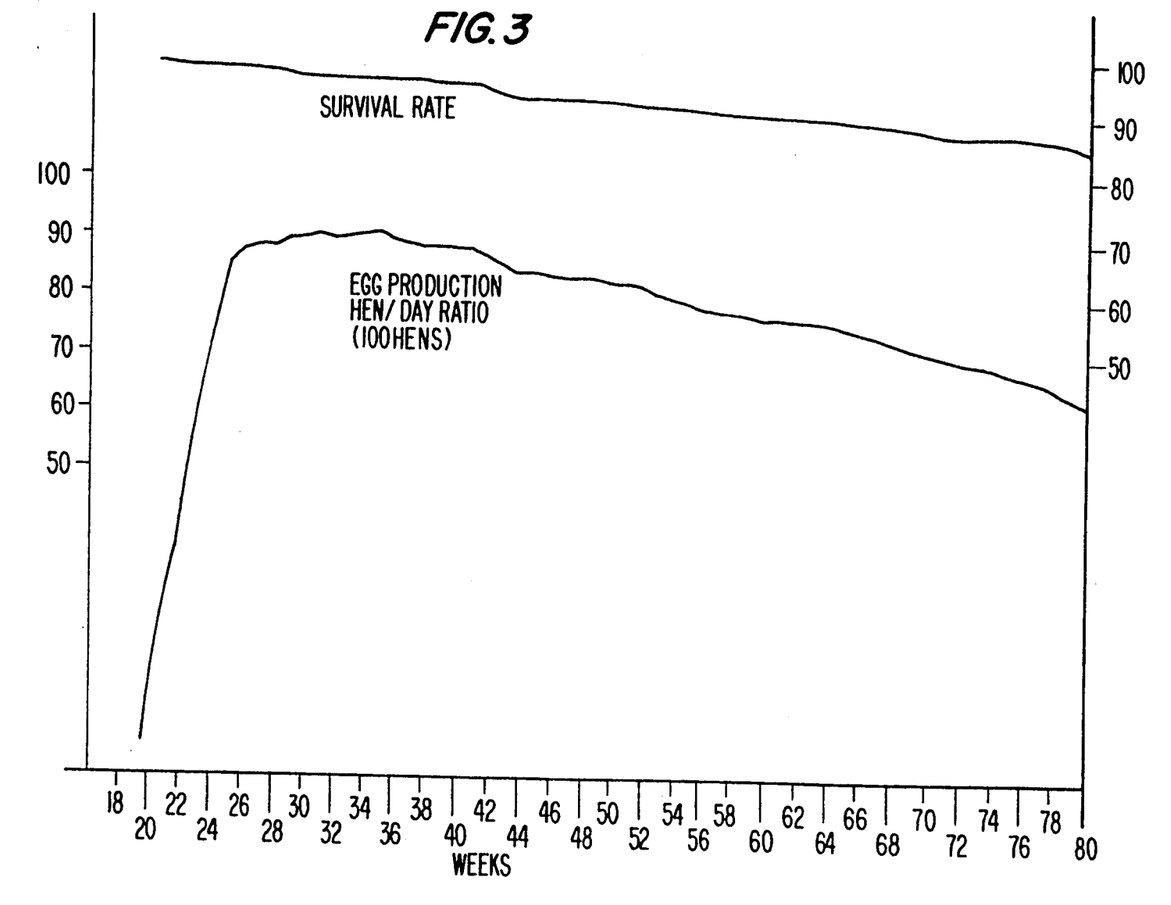
FIG. 3 illustrates graphically the survival rate and egg production of hens fed with a plain poultry feed to which has been added a source of Omega-3 polyunsaturated fatty acids and Vitamin E and separately feeding the hens enriched water in accordance with the method of the present invention.

FIGS. 1, 2 and 3 illustrate, in graphic form, the survival rate and egg production expressed as a hen/day ratio for each of the three groups of hens studied. FIG. 1 shows the number of hens remaining alive of the original 100 and the number of eggs laid by 100 hens per day for the Group 1 hens fed plain feed during the 75 week period. FIG. 2 shows, graphically, the same data for the group 2 hens fed plain feed with the 5% Omega-3 polyunsaturated fatty acids additive, and FIG. 3 sets forth this data for the Group 3 hens fed the Omega-3 polyunsaturated fatty acid- and Vitamin E-containing feed and enriched water according to the present invention.

TABLE I

| | Laying Hens Fed Plain Feed | | | | | | | |
|---|---|---|---|---|---|---|---|---|
| Age | Egg Laying | | Egg Weight | Productivity | | Survival | Feed Consmd | Avrg Bird Wt |
| weeks | Hen/Day % | H/H accm p | gr./pc. | gr./Day | gr. accuml | % | gr. | gr. |
| 19 | 5.0 | | 42.5 | | | | | |
| 20 | 20.4 | 1.40 | 43.0 | 8.77 | 61 | | | |
| 21 | 37.2 | 4.00 | 46.5 | 17.30 | 182 | | | |
| 22 | 55.0 | 7.85 | 49.0 | 26.95 | 371 | 99.8 | 85 | 1,480 |
| 23 | 74.8 | 13.09 | 50.5 | 37.77 | 635 | 99.7 | 88 | |
| 24 | 86.1 | 19.12 | 51.9 | 44.69 | 948 | 99.6 | 94 | 1,570 |
| 25 | 90.0 | 25.42 | 53.1 | 47.79 | 1,283 | 99.6 | 100 | |
| 26 | 90.6 | 31.76 | 54.1 | 49.01 | 1,627 | 99.4 | 106 | 1,610 |
| 27 | 91.7 | 38.18 | 55.0 | 50.44 | 1,980 | 99.3 | 112 | |
| 28 | 92.6 | 44.86 | 55.8 | 51.67 | 2,342 | 99.0 | 112 | 1,680 |
| 29 | 92.0 | 51.10 | 56.6 | 52.07 | 2,706 | 98.8 | 112 | |
| 30 | 91.6 | 57.51 | 57.3 | 52.49 | 3,073 | 98.6 | 112 | 1,720 |
| 31 | 91.3 | 63.90 | 57.9 | 52.86 | 3,443 | 98.4 | 112 | |
| 32 | 91.0 | 70.27 | 58.5 | 53.24 | 3,816 | 98.2 | 112 | 1,770 |
| 33 | 90.8 | 76.63 | 59.0 | 53.57 | 4,191 | 98.1 | 112 | |
| 34 | 91.0 | 83.00 | 59.4 | 54.05 | 4,569 | 98.0 | 112 | 1,770 |
| 35 | 90.8 | 89.34 | 59.8 | 54.18 | 4,943 | 97.7 | 112 | |
| 36 | 90.0 | 95.64 | 60.1 | 54.09 | 5,327 | 97.3 | 112 | 1,772 |
| 37 | 91.0 | 102.01 | 60.4 | 54.96 | 4,712 | 97.2 | 113 | |
| 38 | 89.4 | 108.27 | 60.7 | 54.27 | 6,092 | 97.0 | 113 | 1,772 |
| 39 | 88.9 | 114.49 | 61.0 | 54.23 | 6,472 | 96.8 | 113 | |
| 40 | 90.2 | 120.80 | 61.3 | 55.29 | 6,859 | 96.6 | 112 | 1,774 |
| 41 | 87.7 | 126.94 | 61.5 | 53.94 | 7,257 | 96.4 | 113 | |
| 42 | 87.1 | 133.04 | 61.7 | 53.74 | 7,613 | 96.3 | 112 | 1,774 |
| 43 | 85.0 | 138.99 | 61.9 | 52.62 | 7,981 | 96.1 | 111 | |
| 44 | 86.0 | 145.01 | 62.1 | 53.41 | 8,355 | 95.8 | 113 | 1,775 |
| 45 | 86.0 | 151.03 | 62.3 | 53.78 | 8,731 | 95.6 | 114 | |
| 46 | 84.8 | 156.97 | 62.5 | 53.00 | 9,102 | 95.5 | 114 | 1,775 |
| 47 | 84.2 | 162.86 | 62.7 | 52.79 | 9,472 | 95.2 | 113 | |
| 48 | 84.0 | 168.74 | 62.9 | 52.84 | 9,842 | 95.0 | 113 | 1,776 |
| 49 | 83.0 | 174.55 | 63.1 | 52.37 | 10,209 | 94.9 | 113 | |
| 50 | 83.5 | 180.40 | 63.2 | 52.77 | 10,578 | 94.5 | 112 | 1,776 |
| 51 | 83.6 | 186.25 | 63.4 | 53.00 | 10,949 | 94.4 | 114 | |

TABLE I-continued

Laying Hens Fed Plain Feed

| Age weeks | Egg Laying Hen/Day % | Egg Laying H/H accm p | Egg Weight gr./pc. | Productivity gr./Day | Productivity gr. accuml | Survival % | Feed Consmd gr. | Avrg Bird Wt gr. |
|---|---|---|---|---|---|---|---|---|
| 52 | 81.5 | 192.00 | 63.5 | 51.75 | 11,311 | 94.2 | 113 | 1,776 |
| 53 | 80.9 | 197.66 | 63.7 | 51.53 | 11,672 | 93.9 | 113 | 1,776 |
| 54 | 80.4 | 203.29 | 63.9 | 51.38 | 12,031 | 93.8 | 114 | |
| 55 | 79.0 | 208.82 | 64.0 | 50.56 | 12,386 | 93.6 | 112 | 1,780 |
| 56 | 79.2 | 214.36 | 64.1 | 50.77 | 12,741 | 93.4 | 112 | |
| 57 | 78.6 | 219.86 | 64.3 | 50.54 | 13,095 | 93.1 | 114 | 1,785 |
| 58 | 78.0 | 225.32 | 64.4 | 50.23 | 13,447 | 93.0 | 114 | |
| 59 | 78.1 | 230.79 | 64.5 | 50.37 | 13,800 | 92.7 | 113 | 1,790 |
| 60 | 78.0 | 236.25 | 64.6 | 50.39 | 14,153 | 92.6 | 113 | |
| 61 | 76.4 | 241.60 | 64.7 | 49.43 | 14,499 | 92.3 | 110 | 1,800 |
| 62 | 75.6 | 146.89 | 64.8 | 48.99 | 14,842 | 92.2 | 111 | |
| 63 | 75.0 | 252.14 | 64.9 | 48.68 | 15,182 | 92.0 | 109 | 1,805 |
| 64 | 74.4 | 257.35 | 65.0 | 48.38 | 15,522 | 91.8 | 109 | |
| 65 | 73.8 | 262.52 | 65.1 | 48.04 | 15,858 | 91.6 | 110 | 1,810 |
| 66 | 72.1 | 267.57 | 65.2 | 47.01 | 16,187 | 91.4 | 110 | |
| 67 | 72.6 | 272.65 | 65.2 | 47.34 | 16,518 | 91.2 | 109 | 1,815 |
| 68 | 72.1 | 277.70 | 65.2 | 47.01 | 16,847 | 91.0 | 109 | |
| 69 | 71.6 | 282.71 | 65.3 | 46.75 | 17,174 | 90.8 | 108 | 1,820 |
| 70 | 72.0 | 287.75 | 65.3 | 47.02 | 17,503 | 90.7 | 108 | |
| 71 | 70.5 | 292.69 | 65.4 | 46.11 | 17,826 | 90.5 | 108 | 1,825 |
| 72 | 70.0 | 297.59 | 65.4 | 45.78 | 18,146 | 90.2 | 109 | |
| 73 | 69.4 | 302.45 | 65.5 | 45.46 | 18,464 | 90.1 | 109 | 1,830 |
| 74 | 68.8 | 307.27 | 65.5 | 45.06 | 18,779 | 89.9 | 108 | |
| 75 | 69.0 | 312.10 | 65.5 | 45.20 | 19,095 | 89.6 | 107 | 1,830 |
| 76 | 67.6 | 316.83 | 65.6 | 44.35 | 19,405 | 89.4 | 107 | |
| 77 | 67.0 | 321.52 | 65.6 | 43.95 | 19,713 | 89.2 | 107 | 1,840 |
| 78 | 66.4 | 326.17 | 65.6 | 43.56 | 20,018 | 89.0 | 106 | |
| 79 | 65.8 | 330.78 | 65.7 | 43.23 | 20,321 | 88.8 | 106 | 1,850 |
| 80 | 65.3 | 335.35 | 65.7 | 42.90 | 20,621 | 88.5 | 106 | 1,860 |

TABLE II

Laying Hens Fed Feed With Omega-3 Polyunsaturated Fatty Acid Added

| Age weeks | Egg Laying Hen/Day % | Egg Laying H/H accm p | Egg Weight gr./pc. | Productivity gr./Day | Productivity gr. accuml | Survival % | Feed Consmd gr. | Avrg Bird Wt gr. |
|---|---|---|---|---|---|---|---|---|
| 19 | 5.0 | | 42.5 | | | | | |
| 20 | 20.4 | 1.40 | 43.0 | 8.77 | 61 | | | |
| 21 | 37.2 | 4.00 | 46.5 | 17.30 | 182 | | | |
| 22 | 55.0 | 7.85 | 49.0 | 26.95 | 371 | 99.8 | 85 | 1,480 |
| 23 | 74.8 | 13.07 | 50.5 | 37.77 | 635 | 99.7 | 88 | |
| 24 | 74.7 | 18.28 | 51.9 | 38.77 | 907 | 99.6 | 94 | 1,570 |
| 25 | 73.2 | 23.38 | 53.1 | 38.88 | 1,179 | 99.6 | 100 | |
| 26 | 68.8 | 28.17 | 54.0 | 37.15 | 1,439 | 99.4 | 105 | 1,600 |
| 27 | 68.7 | 32.74 | 54.5 | 37.44 | 1,701 | 95.0 | 103 | |
| 28 | 68.5 | 37.26 | 54.7 | 37.47 | 1,961 | 94.2 | 103 | 1,600 |
| 29 | 69.5 | 41.83 | 55.2 | 38.36 | 2,230 | 94.0 | 103 | |
| 30 | 70.0 | 46.41 | 56.0 | 39.20 | 2,504 | 93.4 | 108 | 1,650 |
| 31 | 68.2 | 50.80 | 56.8 | 38.74 | 2,775 | 92.0 | 108 | |
| 32 | 68.0 | 55.06 | 57.5 | 39.10 | 3,049 | 89.5 | 105 | 1,650 |
| 33 | 67.8 | 59.29 | 58.3 | 39.53 | 3,326 | 89.2 | 110 | |
| 34 | 68.5 | 63.54 | 59.0 | 40.42 | 3,609 | 89.1 | 110 | 1,680 |
| 35 | 67.6 | 67.74 | 59.3 | 40.09 | 3,890 | 88.3 | 110 | |
| 36 | 67.6 | 71.71 | 60.0 | 40.56 | 4,174 | 87.9 | 105 | 1,690 |
| 37 | 68.2 | 75.88 | 59.6 | 46.65 | 4,501 | 87.3 | 105 | |
| 38 | 70.0 | 80.14 | 60.1 | 42.07 | 4,796 | 87.0 | 103 | 1,700 |
| 39 | 71.3 | 84.44 | 60.5 | 43.14 | 5,097 | 86.2 | 103 | |
| 40 | 70.2 | 88.62 | 60.8 | 42.68 | 5,394 | 85.0 | 103 | 1,705 |
| 41 | 68.0 | 92.59 | 61.0 | 41.48 | 5,684 | 83.5 | 108 | |
| 42 | 67.5 | 96.51 | 61.2 | 41.31 | 5,973 | 83.0 | 108 | 1,710 |
| 43 | 67.7 | 100.41 | 61.3 | 41.50 | 6,264 | 82.3 | 108 | |
| 44 | 66.5 | 104.21 | 61.4 | 40.83 | 6,550 | 81.6 | 108 | 1,713 |
| 45 | 66.0 | 107.88 | 61.4 | 40.52 | 6,834 | 79.0 | 110 | |
| 46 | 65.1 | 111.41 | 60.8 | 39.58 | 7,111 | 77.9 | 110 | 1,715 |
| 47 | 65.2 | 114.95 | 60.8 | 39.64 | 7,388 | 77.5 | 110 | |
| 48 | 65.7 | 118.49 | 61.0 | 40.08 | 7,669 | 77.0 | 108 | 1,738 |
| 49 | 65.0 | 121.94 | 61.1 | 39.72 | 7,947 | 75.9 | 108 | |
| 50 | 64.6 | 125.36 | 61.4 | 39.66 | 8,225 | 75.6 | 108 | 1,743 |
| 51 | 63.5 | 128.70 | 61.6 | 39.12 | 8,499 | 75.2 | 105 | |
| 52 | 63.0 | 131.99 | 62.1 | 39.12 | 8,773 | 74.5 | 105 | 1,745 |
| 53 | 63.0 | 135.20 | 62.3 | 39.25 | 9,048 | 72.8 | 107 | |
| 54 | 61.5 | 138.33 | 62.5 | 38.44 | 9,317 | 72.6 | 107 | 1,752 |
| 55 | 62.3 | 141.45 | 62.5 | 38.94 | 9,590 | 71.5 | 107 | |
| 56 | 60.0 | 144.39 | 62.6 | 37.56 | 9,853 | 70.0 | 104 | 1,755 |
| 57 | 58.6 | 147.24 | 62.7 | 36.74 | 10,110 | 69.6 | 104 | |
| 58 | 58.1 | 150.05 | 63.0 | 36.60 | 10,366 | 69.2 | 104 | 1,758 |

TABLE II-continued

Laying Hens Fed Feed With Omega-3 Polyunsaturated Fatty Acid Added

| Age weeks | Egg Laying Hen/Day % | Egg Laying H/H accm p | Egg Weight gr./pc. | Productivity gr./Day | Productivity gr. accuml | Survival % | Feed Consmd gr. | Avrg Bird Wt gr. |
|---|---|---|---|---|---|---|---|---|
| 59 | 57.5 | 152.79 | 63.1 | 36.28 | 10,620 | 68.1 | 100 | |
| 60 | 55.5 | 155.43 | 63.4 | 35.19 | 10,866 | 67.9 | 100 | 1,760 |
| 61 | 55.5 | 158.01 | 63.6 | 35.30 | 11,113 | 66.3 | 98 | |
| 62 | 56.4 | 160.60 | 63.6 | 35.87 | 11,364 | 65.7 | 98 | 1,766 |
| 63 | 56.6 | 163.18 | 63.7 | 36.05 | 11,616 | 65.2 | 98 | |
| 64 | 55.5 | 165.63 | 64.2 | 35.63 | 11,865 | 63.1 | 97 | 1,768 |
| 65 | 55.0 | 168.05 | 64.2 | 35.31 | 12,112 | 62.8 | 97 | |
| 66 | 54.2 | 170.36 | 64.3 | 34.85 | 12,356 | 60.9 | 95 | 1,770 |
| 67 | 53.9 | 172.62 | 64.4 | 34.71 | 12,599 | 60.0 | 95 | |
| 68 | 53.0 | 174.83 | 64.4 | 34.13 | 12,838 | 59.6 | 95 | 1,773 |
| 69 | 53.0 | 176.56 | 64.5 | 34.19 | 13,077 | 57.3 | 93 | |
| 70 | 52.6 | 178.64 | 64.5 | 33.93 | 13,315 | 56.4 | 93 | 1,773 |
| 71 | 51.5 | 180.65 | 65.0 | 33.48 | 13,549 | 55.7 | 90 | |
| 72 | 50.0 | 182.58 | 65.0 | 32.50 | 13,777 | 55.0 | 90 | 1,700 |
| 73 | 47.5 | 184.34 | 65.0 | 30.86 | 13,993 | 53.0 | 90 | |
| 74 | 45.0 | 185.99 | 65.2 | 29.34 | 14,198 | 52.5 | 90 | 1,700 |
| 75 | 43.7 | 187.57 | 65.2 | 28.49 | 14,397 | 51.5 | 90 | |
| 76 | | | | | | | | |
| 77 | | | | | | | | |
| 78 | | | | | | | | |
| 79 | | | | | | | | |
| 80 | | | | | | | | |

TABLE III

Laying Hens Fed Feed With Omega-3 Polyunsaturated Fatty Acid and Enriched Water Added

| Age weeks | Egg Laying Hen/Day % | Egg Laying H/H accm p | Egg Weight gr./pc. | Productivity gr./Day | Productivity gr. accuml | Survival % | Feed Consmd gr. | Avrg Bird Wt gr. |
|---|---|---|---|---|---|---|---|---|
| 19 | 5.0 | | 42.6 | | | | | |
| 20 | 20.4 | 1.40 | 42.9 | 8.75 | 61 | | | |
| 21 | 37.2 | 4.00 | 47.1 | 17.52 | 184 | | | |
| 22 | 55.0 | 7.85 | 49.3 | 27.12 | 374 | 99.8 | 84 | 1,481 |
| 23 | 74.8 | 13.09 | 50.4 | 37.70 | 638 | 99.7 | 87 | |
| 24 | 86.1 | 19.12 | 51.8 | 44.60 | 950 | 99.6 | 95 | 1,573 |
| 25 | 89.5 | 25.39 | 53.5 | 47.88 | 1,285 | 99.6 | 103 | |
| 26 | 89.0 | 31.62 | 54.1 | 48.15 | 1,622 | 99.4 | 105 | 1,615 |
| 27 | 90.6 | 37.96 | 55.1 | 49.92 | 1,971 | 98.1 | 110 | |
| 28 | 90.4 | 44.29 | 55.6 | 50.26 | 2,323 | 97.5 | 110 | 1,685 |
| 29 | 91.2 | 50.67 | 56.5 | 51.53 | 2,684 | 97.5 | 110 | |
| 30 | 90.5 | 57.01 | 57.0 | 51.59 | 3,045 | 97.4 | 110 | 1,728 |
| 31 | 90.7 | 63.36 | 57.1 | 51.79 | 3,408 | 97.3 | 113 | |
| 32 | 91.0 | 69.73 | 58.0 | 52.78 | 3,777 | 97.2 | 113 | 1,730 |
| 33 | 91.4 | 76.13 | 58.8 | 53.74 | 4,153 | 97.0 | 115 | |
| 34 | 90.0 | 82.43 | 59.1 | 53.19 | 4,525 | 97.0 | 115 | 1,750 |
| 35 | 89.5 | 88.70 | 59.4 | 53.16 | 4,897 | 96.9 | 115 | |
| 36 | 88.7 | 94.91 | 59.9 | 53.13 | 5,269 | 96.9 | 116 | 1,770 |
| 37 | 88.4 | 101.10 | 60.1 | 53.13 | 5,641 | 96.6 | 117 | |
| 38 | 88.0 | 107.26 | 60.5 | 53.24 | 6,014 | 96.3 | 117 | 1,778 |
| 39 | 88.0 | 113.42 | 60.8 | 53.50 | 6,389 | 96.1 | 117 | |
| 40 | 87.5 | 119.55 | 60.8 | 53.20 | 6,761 | 96.0 | 117 | 1,782 |
| 41 | 86.2 | 125.58 | 61.0 | 52.58 | 7,129 | 95.0 | 116 | |
| 42 | 85.0 | 131.53 | 61.3 | 52.11 | 7,494 | 94.8 | 116 | 1,785 |
| 43 | 85.0 | 137.48 | 61.4 | 52.19 | 8,159 | 94.7 | 114 | |
| 44 | 84.7 | 143.41 | 61.6 | 52.18 | 8,524 | 94.7 | 114 | 1,787 |
| 45 | 84.1 | 149.30 | 61.8 | 51.97 | 8,888 | 94.6 | 115 | |
| 46 | 84.0 | 155.18 | 62.0 | 52.08 | 9,253 | 94.6 | 115 | 1,787 |
| 47 | 84.0 | 161.06 | 62.4 | 52.42 | 9,620 | 94.6 | 116 | |
| 48 | 83.6 | 166.91 | 62.6 | 52.33 | 9,986 | 94.4 | 116 | 1,790 |
| 49 | 83.5 | 172.76 | 63.0 | 52.61 | 10,354 | 94.0 | 116 | |
| 50 | 83.4 | 178.60 | 63.0 | 52.54 | 10,722 | 93.9 | 117 | 1,793 |
| 51 | 82.6 | 184.38 | 63.1 | 52.12 | 11,087 | 93.8 | 115 | |
| 52 | 82.1 | 190.13 | 63.2 | 51.89 | 11,450 | 93.7 | 115 | 1,793 |
| 53 | 80.7 | 195.78 | 63.4 | 51.16 | 11,808 | 93.6 | 116 | |
| 54 | 79.9 | 201.37 | 63.6 | 50.82 | 12,164 | 93.6 | 116 | 1,796 |
| 55 | 77.4 | 206.79 | 63.8 | 49.38 | 12,510 | 93.3 | 115 | |
| 56 | 77.0 | 212.18 | 63.9 | 49.20 | 12,854 | 92.8 | 115 | 1,798 |
| 57 | 75.8 | 217.49 | 63.7 | 48.28 | 13,192 | 92.5 | 116 | |
| 58 | 75.4 | 222.77 | 63.8 | 48.11 | 13,529 | 92.5 | 116 | 1,800 |
| 59 | 75.8 | 228.08 | 64.0 | 48.51 | 13,869 | 91.7 | 117 | |
| 60 | 76.6 | 233.44 | 64.4 | 49.33 | 14,143 | 91.6 | 117 | 1,803 |
| 61 | 76.5 | 238.80 | 64.6 | 49.42 | 14,489 | 91.5 | 115 | |
| 62 | 76.0 | 244.12 | 64.7 | 49.17 | 14,833 | 91.3 | 115 | 1,806 |
| 63 | 75.8 | 249.43 | 64.9 | 49.19 | 15,177 | 90.9 | 114 | |
| 64 | 75.7 | 254.73 | 65.0 | 49.21 | 15,521 | 90.7 | 114 | 1,808 |

TABLE III-continued

Laying Hens Fed Feed With Omega-3
Polyunsaturated Fatty Acid and Enriched Water Added

| Age weeks | Egg Laying Hen/Day % | Egg Laying H/H accm p | Egg Weight gr./pc. | Productivity gr./Day | Productivity gr. accuml | Survival % | Feed Consmd gr. | Avrg Bird Wt gr. |
|---|---|---|---|---|---|---|---|---|
| 65 | 75.0 | 259.98 | 64.9 | 48.68 | 15,868 | 90.4 | 113 | |
| 66 | 74.6 | 265.20 | 65.0 | 48.49 | 16,207 | 90.0 | 113 | 1,812 |
| 67 | 73.9 | 270.37 | 65.1 | 48.11 | 16,544 | 89.9 | 112 | |
| 68 | 73.4 | 275.51 | 65.2 | 47.86 | 16,879 | 89.6 | 112 | 1,818 |
| 69 | 73.0 | 280.62 | 65.3 | 47.67 | 17,213 | 88.8 | 110 | |
| 70 | 72.8 | 285.72 | 65.4 | 47.61 | 17,546 | 88.4 | 110 | 1,823 |
| 71 | 71.4 | 290.72 | 65.5 | 46.77 | 17,873 | 87.9 | 109 | |
| 72 | 69.9 | 295.61 | 65.5 | 45.78 | 18,193 | 87.8 | 109 | 1,828 |
| 73 | 69.3 | 300.44 | 65.6 | 45.46 | 18,511 | 87.8 | 107 | |
| 74 | 69.1 | 305.27 | 65.7 | 45.40 | 18,829 | 87.8 | 107 | 1,834 |
| 75 | 68.5 | 310.07 | 65.7 | 45.00 | 19,144 | 87.6 | 106 | |
| 76 | 68.0 | 314.83 | 65.7 | 44.68 | 19,457 | 87.4 | 106 | 1,838 |
| 77 | 67.4 | 319.55 | 65.8 | 44.35 | 19,767 | 87.3 | 105 | |
| 78 | 65.9 | 324.16 | 65.8 | 43.36 | 20,071 | 87.2 | 105 | 1,843 |
| 79 | 64.1 | 328.65 | 65.8 | 42.18 | 20,366 | 87.0 | 105 | |
| 80 | 63.3 | 333.08 | 65.9 | 41.71 | 20,658 | 86.8 | 104 | 1,855 |

A comparison of the data in FIGS. 1 and 2 and in Tables I and II above demonstrate that feeding hens plain feed to which Omega-3 polyunsaturated fatty acids have been added lowered egg production and increased mortality. At 75 weeks, the survival rate of the Group 1 hens fed plain feed was 89.6%; almost 90 of the 100 birds were still alive. The 75 week survival rate for the Group 2 hens fed Omega-3 acids was 51.5%. Almost half of the original group had died. Of the Group 2 hens that survived, moreover, not only were the feed consumption and body weight lower, but also the number of eggs laid was lower, and the eggs were lighter in weight.

The accumulated piece number of eggs and the accumulated weight of the eggs during the 75 weeks for the Group 2 hens can be compared as follows:

<312.10:187.57 pcs>(60.10%)

<19,095:14,397 gr.>(75.40%)

This means that the Omega-3 polyunsaturated fatty acid-fed hens of Group 2, as each week passed, produced fewer eggs. This can be seen by comparing the survival rate x accumulated produced pieces as follows:

30th week: 46.41/57.51×93.4/98.6=76.4%

50th week: 125.36/180.40×75.6/94.5=55.6%

70th week: 178.64/287.75×96.4/90.7=38.6%

75th week: 187.57/312.10×51.5/89.6=34.5%

This decrease in productivity clearly shows that the addition of only Omega-3 polyunsaturated fatty acids to feed, without more, may initially have little or no effect on egg production, but that it has a decidedly adverse effect on egg production over a period of time. This evidence, in addition, generally demonstrates the adverse effect on the production of commercially useful quantities of eggs which can result from feeding an excess amount of a particular nutrient so that the diet is unbalanced, and specifically demonstrates the adverse effects on commercial egg production resulting from a diet containing an excess of Omega-3 polyunsaturated fatty acids.

The method of the present invention avoids the nutritional imbalance which results from feeding hens excessive amounts of Omega-3 polyunsaturated fatty acids by adding Vitamin E to the feed and by concurrently and separately feeding the enriched water as described above. The hens fed the Omega-3 fatty acids and the enriched water stayed healthy and, thus, were capable of the egg production demonstrated by the data in Table III. The hens fed only the Omega-3 polyunsaturated fatty acids, on the other hand, demonstrated not only higher mortality and lower egg production, but also displayed molting, abnormal digestion, loss of appetite and body weight and were generally dull and inactive. A comparison of survival rates and egg production for Groups 1, 2 and 3 is set forth in Tables IV and V below. The data from Group 3, which was fed Omega-3 polyunsaturated fatty acids and, separately, the enriched water appears between the other two groups. This data clearly demonstrates that feeding the hens a diet of Omega-3 polyunsaturated fatty acid and Vitamin E-containing feed and, separately, the enriched water described herein results in a survival rate and egg production similar to those of hens fed with plain commercial feed.

TABLE IV

| | SURVIVAL RATE | | | | | |
|---|---|---|---|---|---|---|
| | 25 Week | 35 Week | 45 Week | 55 Week | 65 Week | 75 Week |
| Group 1 (%) | 99.6 (100.-) | 97.7 (100.-) | 95.6 (100.-) | 93.6 (100.-) | 91.6 (100.-) | 89.6 (100.-) |
| Group 3 (%) | 99.6 (100.-) | 96.9 (99.18) | 94.6 (98.95) | 93.3 (99.68) | 90.4 (98.69) | 87.6 (97.77) |
| Group 2 (%) | 99.6 (100.-) | 88.3 (90.38) | 79.0 (82.64) | 71.5 (76.39) | 62.8 (68.56) | 51.5 (57.48) |

TABLE V

| | EGG PRODUCTION (HEN/DAY-PIECE) | | | | | |
|---|---|---|---|---|---|---|
| | 25 Week | 35 Week | 45 Week | 55 Week | 65 Week | 75 Week |
| Group 1 (%) | 25.42 (100.-) | 89.34 (100.-) | 151.03 (100.-) | 208.82 (100.-) | 262.52 (100.-) | 312.10 (100.-) |
| Group 3 (%) | 25.39 (99.88) | 88.70 (99.28) | 149.30 (98.85) | 206.79 (99.03) | 259.98 (99.03) | 310.07 (99.35) |
| Group 2 (%) | 23.38 (91.97) | 67.74 (75.82) | 107.86 (71.42) | 141.45 (67.74) | 168.05 (64.01) | 187.57 (60.10) |

Actual productivity, for commercial purposes, is a combination of laying capacity and survival. The laying capacity of the Groups 2 and 3 hens was calculated and compared to demonstrate further the remarkable improvement achieved by feeding the hens enriched water according to the present invention. The laying capacity was determined by the product of survival rate and the accumulated produced pieces. The results are set forth in Table VI below.

TABLE VI

| | EGG LAYING CAPACITY | |
|---|---|---|
| | Group 3 | Group 2 |
| 30th week: | 57.01/57.51 × 97.4/98.6 = 97.9% | 76.4% |
| 50th week: | 178.60/180.40 × 93.9/94.5 = 98.4% | 55.6% |
| 70th week: | 285.72/287.75 × 88.4/90.7 = 96.8% | 38.6% |
| 75th week: | 310.07/312.10 × 87.6/89.6 = 97.1% | 34.5% |

Tables I to VI and FIGS. 1 to 3 clearly demonstrate the beneficial effects achieved on a commercial scale of the poultry feeding method of the present invention. The simultaneous feeding of hens of an excessive amount of Omega-3 polyunsaturated fatty acids and, separately, a supply of enriched water results in a hen survival rate and egg production rate which resembles that of hens red ordinary feed rather than that of hens fed the same excess of Omega-3 polyunsaturated fatty acids, but without the enriched water. In addition, this method makes possible the commercial production of eggs with increased concentrations of Omega-3 polyunsaturated fatty acids.

Although the present invention has been described in detail with respect to the commercial production of high Omega-3 polyunsaturated fatty acid-containing poultry eggs, the present method can also be employed to produce, on a commercial basis, economically profitable numbers of meat-producing fowl with increased Omega-3 polyunsaturated fatty acids in the meat. The survival rate for broilers fed with feed to which has been added Omega-3 polyunsaturated fatty acids and concurrently with a separate supply of enriched water as described herein parallels that of the laying hens fed the same feed. Consequently, the present feeding method can be employed to produce consumer acceptable high Omega-3 polyunsaturated fatty acid-containing poultry meat as well as consumer acceptable high Omega-3 polyunsaturated fatty acid-containing poultry eggs.

INDUSTRIAL APPLICABILITY

The method of the present invention will find its primary applicability in the production of poultry products containing increased amounts of Omega-3 polyunsaturated fatty acids for consumption by consumers who wish to avail themselves of the beneficial effects of Omega-3 polyunsaturated fatty acids. However, the present method could also be used to feed animals other than poultry, such as, for example, cattle and pigs, to produce beef, pork and even milk with increased concentrations of Omega-3 polyunsaturated fatty acids.

We claim:

1. A method for producing commercially valuable quantities of poultry products high in Omega-3 polyunsaturated fatty acids comprising feeding poultry a poultry feed containing about 1 to 5% by weight of Omega-3 polyunsaturated fatty acids and Vitamin E and concurrently feeding to the poultry a separate supply of an enriched water containing at least silicic acid, glucanase, cellulase, calcium and phosphorus in amounts effective to insure a sufficiently high survival rate of the poultry to produce commercially useful quantities of said poultry products.

2. The method described in claim 1, wherein 120 grams of said enriched water is fed to each bird per day.

3. The method described in claim 2, wherein said enriched water contains 0.369% silicic acid, 0.018% glucanase, 0.004% cellulase, 0.006% calcium and 0.001% phosphorus.

4. The method described in claim 1, wherein Vitamin E is added to said feed at about 0.7% by weight of said feed.

5. A method for producing a commercially useful supply of chicken eggs containing at least 0.5 gram of Omega-3 polyunsaturated fatty acids in each 100 grams of yolk comprising concurrently feeding laying hens feed containing about 5% by weight Omega-3 polyunsaturated fatty acids, Vitamin E and a separate supply of enriched water containing at least silicic acid, glucanase, cellulase, calcium and phosphorus in amounts effective to insure a sufficiently high survival rate of the hens to produce commercially useful quantities of eggs.

6. The method described in claim 5, wherein said feed contains 0.7% by weight of Vitamin E.

7. The method described in claim 5, wherein 120 grams of said enriched water is fed to each hen each day.

8. The method described i claim 5, wherein said enriched water contains 0.369% silicic acid, 0.018% glucanase, 0.004% cellulase, 0.006% calcium and 0.001% phosphorus.

9. A method for producing a dependable, commercially useful supply of chicken eggs containing at least 0.5 gram of Omega-3 polyunsaturated fatty acids per 100 grams of yolk comprising feeding laying hens feed containing about 5% by weight Omega-3 polyunsaturated fatty acids and 0.7% by weight Vitamin E concurrently with 120 grams per day per hen of water from a supply of water enriched with at least silicic acid, glucanase, cellulase, calcim and phosphorus.

* * * * *